United States Patent
Masuda et al.

(10) Patent No.: US 11,697,781 B2
(45) Date of Patent: Jul. 11, 2023

(54) IONIC LIQUID INCLUDING FLUORINE-CONTAINING PHOSPHATE ESTER ANIONS, AND LUBRICATING OIL COMPOSITION

(71) Applicants: Nisshinbo Holdings Inc., Tokyo (JP); UNIMATEC CO., LTD., Tokyo (JP)

(72) Inventors: Gen Masuda, Chiba (JP); Keisuke Kokin, Kitaibaraki (JP)

(73) Assignees: NISSHINBO HOLDINGS INC., Tokyo (JP); UNIMATEC CO., LTD., Tokyo (JP)

(*) Notice: Subject to any disclaimer, the term of this patent is extended or adjusted under 35 U.S.C. 154(b) by 0 days.

(21) Appl. No.: 17/916,875

(22) PCT Filed: Mar. 5, 2021

(86) PCT No.: PCT/JP2021/008747
§ 371 (c)(1),
(2) Date: Oct. 4, 2022

(87) PCT Pub. No.: WO2021/205795
PCT Pub. Date: Oct. 14, 2021

(65) Prior Publication Data
US 2023/0159842 A1    May 25, 2023

(30) Foreign Application Priority Data
Apr. 6, 2020    (JP) .................................. 2020-068222

(51) Int. Cl.
*C10M 105/74* (2006.01)
*C07F 9/40* (2006.01)
*C10N 20/00* (2006.01)

(52) U.S. Cl.
CPC .......... *C10M 105/74* (2013.01); *C07F 9/4006* (2013.01); *C10M 2223/043* (2013.01); *C10M 2223/0603* (2013.01); *C10N 2020/077* (2020.05)

(58) Field of Classification Search
CPC .......... C10M 105/74; C10M 2223/043; C10M 2223/0603; C10N 2020/077; C07F 9/4006
See application file for complete search history.

(56) References Cited

U.S. PATENT DOCUMENTS

| | | | | |
|---|---|---|---|---|
| 3,492,374 A * | 1/1970 | Le Bleu | ................ | C14C 9/00 544/110 |
| 2007/0179263 A1 * | 8/2007 | Koh | ................ | C07D 239/42 526/248 |
| 2008/0221361 A1 * | 9/2008 | Walker | ................ | C07C 217/28 564/508 |

FOREIGN PATENT DOCUMENTS

JP    61-120898 A    6/1986
JP    2008-291231 A    12/2008
(Continued)

OTHER PUBLICATIONS

"The Science of ionic liquids—Toward a new generation of liquids", Maruzen Publishing, 2012, pp. 317-322, cited in Specification, w/English translation (21 pages).
(Continued)

*Primary Examiner* — Vishal V Vasisth
(74) *Attorney, Agent, or Firm* — WHDA, LLP

(57) ABSTRACT

Provided are: an ionic liquid including the fluorine-containing phosphate ester anions represented by formula (1); and a lubricating oil composition including said ionic liquid.
(Continued)

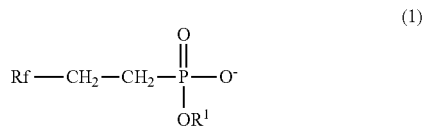

(1)

(In the formula, Rf represents a C1-14 perfluoroalkyl group. $R^1$ represents a C1-8 alkyl group.)

12 Claims, 13 Drawing Sheets

(56) References Cited

FOREIGN PATENT DOCUMENTS

| | | |
|---|---|---|
| JP | 2009-57541 A | 3/2009 |
| JP | 2014-12666 A | 1/2014 |
| JP | 2014-15505 A | 1/2014 |
| WO | WO-2006057272 A1 * 6/2006 | ............ C07F 9/4006 |

OTHER PUBLICATIONS

"Ionic liquid technology", Toray Research Center, 2013, pp. 67-73, cited in Specification, w/English translation (18 pages).
International Search Report dated Jun. 1, 2021, issued in counterpart International Application No. PCT/JP2021/008747 (2 pages).

* cited by examiner

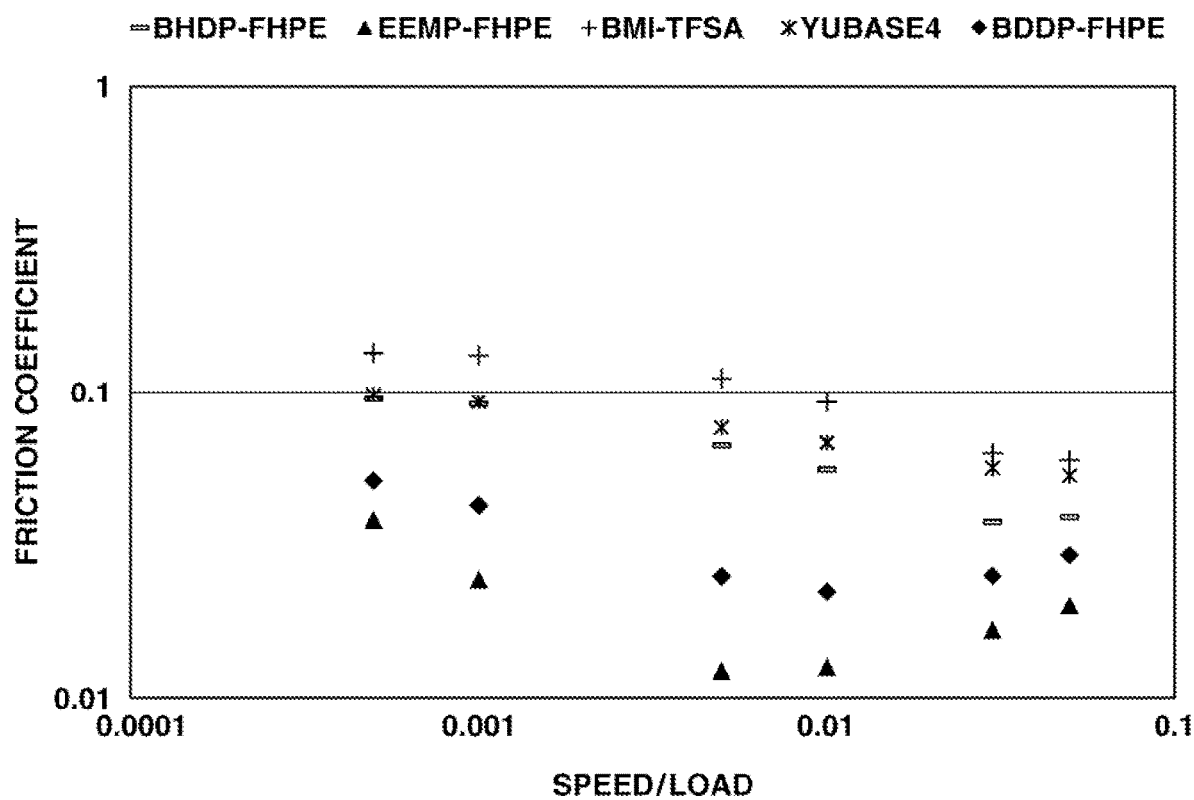

IONIC LIQUID INCLUDING FLUORINE-CONTAINING PHOSPHATE ESTER ANIONS, AND LUBRICATING OIL COMPOSITION

DESCRIPTION

This application is a 371 of PCT/JP2021/008747 filed Mar. 5, 2021.

TECHNICAL FIELD

This invention relates to an ionic liquid which includes fluorine-containing phosphate ester anions, and to a lubricating oil composition.

BACKGROUND ART

The term 'ionic liquid' refers to a salt composed solely of ions which typically has a melting point of 100° C. or below. Ionic liquids are the subject of various ongoing applied research on account of their properties. Given such properties as non-volatility, flame retardancy and high heat resistance in particular, research is even being conducted on the practical use of ionic liquids as lubricants (see, for example, Patent Documents 1 and 2, and Non-Patent Documents 1 and 2).

Ionic liquids have the physicochemical qualities required of a lubricant. In particular, fluorine-containing ionic liquids such as tetrafluoroborate, hexafluorophosphate and bis(trifluoromethanesulfonyl)imide salts reportedly have excellent friction performances. However, further improvements in performance have been desired.

PRIOR ART DOCUMENTS

PATENT DOCUMENTS

Patent Document 1: JP-A 2009-57541
Patent Document 2: JP-A 2014-15505

NON-PATENT DOCUMENTS

Non-Patent Document 1: *Ion Ekitai no Kagaku-Shinsedai Ekitai e no Chōsen* [The Science of ionic liquids-Toward a new generation of liquids], Maruzen Publishing (2012), pp. 317-322.
Non-Patent Document 2: *Ion Ekitai Takunorojii* [Ionic liquid technology], Toray Research Center (2013), pp. 67-73.

SUMMARY OF INVENTION

Technical Problem

It is therefore an object of the present invention to provide an ionic liquid which exhibits a friction performance superior to that of conventional fluorine-containing ionic liquids and is useful as a lubricant. Another object is to provide a lubricating oil composition containing the same.

Solution to Problem

The inventors have conducted intensive investigations aimed at achieving the above object. As a result, they have discovered that ionic liquids which include fluorine-containing phosphate ester anions have a low friction coefficient and are suitable as the base oil of lubricating oil compositions.

Accordingly, the invention provides the following ionic liquid and lubricating oil composition.

1. An ionic liquid which includes fluorine-containing phosphate ester anions of formula (1) below.
[Chem. 1]

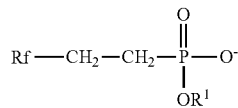

(1)

(wherein Rf is a perfluoroalkyl group of 1 to 14 carbon atoms, and $R^1$ is an alkyl group of 1 to 8 carbon atoms or an aromatic hydrocarbon group of 6 to 10 carbon atoms).

2. The ionic liquid of 1 above, wherein Rf is a linear perfluoroalkyl group of 1 to 14 carbon atoms.

3. The ionic liquid of 2 above, wherein Rf is a perfluoroethyl, perfluoro-n-butyl, perfluoro-n-hexyl, perfluoro-n-octyl, perfluoro-n-decyl, perfluoro-n-dodecyl or perfluoro-n-tetradecyl group.

4. The ionic liquid of any of 1 to 3 above, wherein $R^1$ is an alkyl group of 1 to 4 carbon atoms.

5. The ionic liquid of any of 1 to 3 above, wherein $R^1$ is a group of 6 to 8 carbon atoms which includes a phenyl group.

6. The ionic liquid of any of 1 to 5 above, wherein the ionic liquid further includes phosphorus atom-containing cations.

7. The ionic liquid of any of 1 to 5 above, wherein the ionic liquid further includes nitrogen atom-containing cations.

8. The ionic liquid of any of 1 to 7 above which has a melting point of 50° C. or below.

9. The ionic liquid of 8 above, wherein the melting point is 25° C. or below.

10. A lubricating oil composition that includes the ionic liquid of any of 1 to 9 above.

11. The lubricating oil composition of 10 above, wherein the ionic liquid serves as a base oil.

12. The lubricating oil composition of 11 above, further including at least one type of additive selected from the group consisting of oxidation inhibitors, antifoam agents, demulsifying agents, emulsifying agents, preservatives, viscosity index improvers, pour point depressants, oiliness agents, antiwear agents, extreme pressure agents, friction modifiers, detergents, dispersants, rust preventives, corrosion inhibitors, colorants and fragrances.

Advantageous Effects of Invention

The ionic liquid of the invention has a low friction coefficient and can be suitably used as a base oil in lubricating compositions. Moreover, it may also be employed in other applications in which ionic liquids can be used, such as reaction solvents and electrolyte solvents.

BRIEF DESCRIPTION OF DRAWINGS

FIG. 13 is a graph showing the relationship among the friction coefficients of the ionic liquids in Examples 1 to 3, and the ionic liquid and YUBASE4 in the Comparative Examples.

DESCRIPTION OF EMBODIMENT

[Ionic Liquid]

Figure 1:
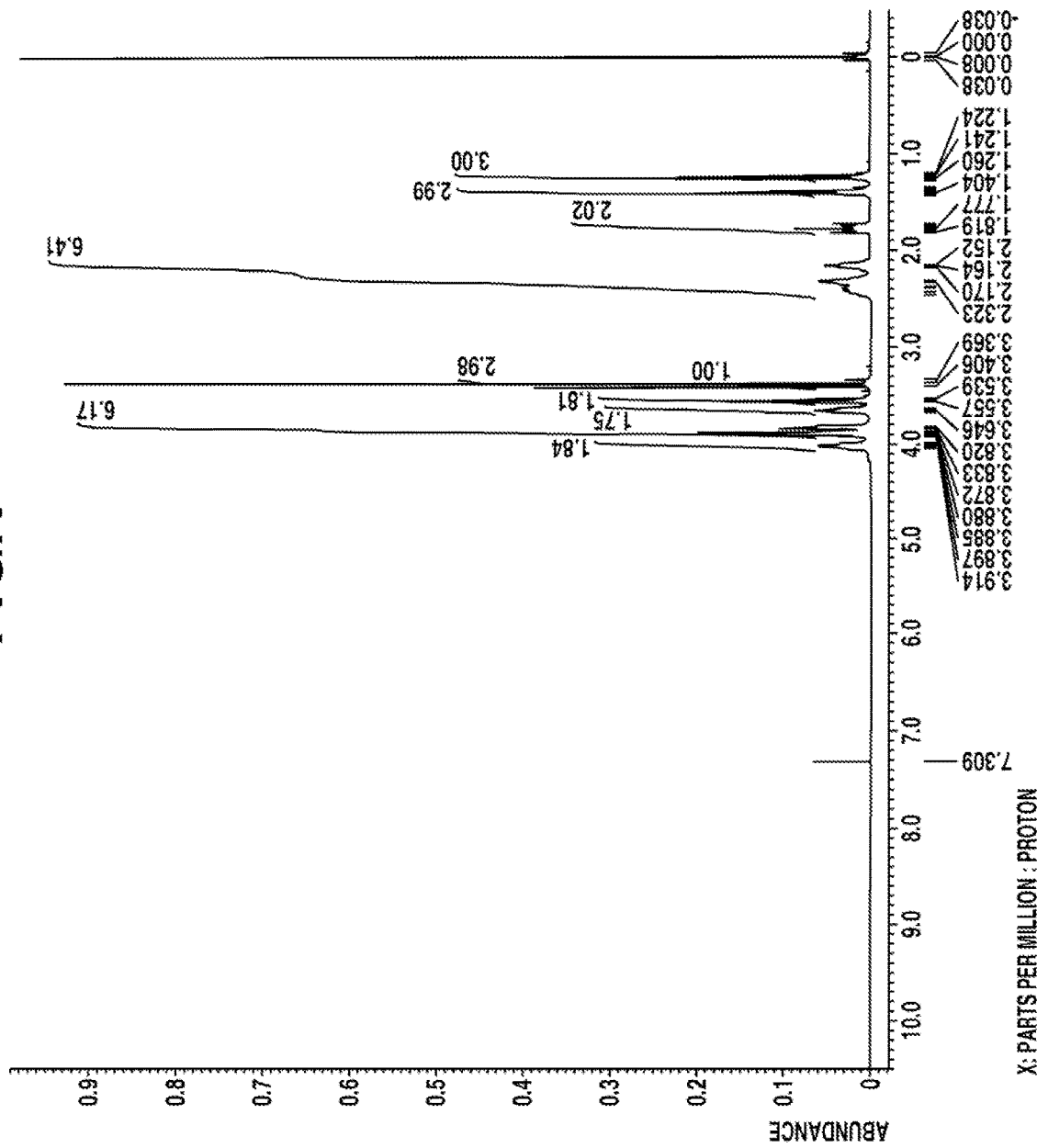
FIG. 1 is a $^1$H-NMR spectrum of EMEP·FHP-E produced in Example 1.

The ionic liquid of the invention includes fluorine-containing phosphate ester anions of formula (1) below. In this invention, "ionic liquid" refers to a salt composed solely of ions. The salt has a melting point of 100° C. or below, preferably 50° C. or below, and more preferably 25° C. or below.

[Chem.2]

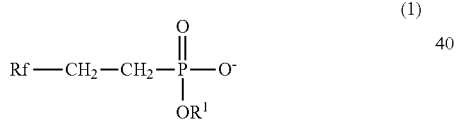

(1)

In formula (1), Rf is a perfluoroalkyl group of 1 to 14 carbon atoms and R$^1$ is an alkyl group of 1 to 8 carbon atoms or an aromatic hydrocarbon group of 6 to 10 carbon atoms.

The perfluoroalkyl group represented by Rf is an alkyl group of 1 to 14 carbon atoms in which all of the hydrogen atoms have been substituted with fluorine atoms. The alkyl group of 1 to 14 carbon atoms may be linear, branched or cyclic. Specific examples include methyl, ethyl, n-propyl, isopropyl, cyclopropyl, n-butyl, s-butyl, isobutyl, t-butyl, cyclobutyl, n-pentyl, isopentyl, s-pentyl, 3-pentyl, neopentyl, t-pentyl, cyclopentyl, n-hexyl, cyclohexyl, n-heptyl, n-octyl, 2-ethylhexyl, n-nonyl, n-decyl, n-undecyl, n-dodecyl, n-tridecyl and n-tetradecyl groups.

Specific examples of the perfluoroalkyl group represented by Rf include the aforementioned alkyl groups of 1 to 14 carbon atoms in which all of the hydrogen atoms have been substituted with fluorine atoms. Of these, linear perfluoroalkyl groups are preferred, with perfluoroethyl, perfluoro-n-butyl, perfluoro-n-hexyl, perfluoro-n-octyl, perfluoro-n-decyl, perfluoro-n-dodecyl and perfluoro-n-tetradecyl groups being more preferred.

The alkyl group of 1 to 8 carbon atoms represented by R$^1$ may be linear, branched or cyclic. Specific examples include, of the alkyl groups of 1 to 14 carbon atoms mentioned above, those having from 1 to 8 carbon atoms. Of these, the alkyl group represented by R$^1$ is preferably an alkyl group of 1 to 4 carbon atoms, more preferably a linear alkyl group of 1 to 4 carbon atoms, and even more preferably an ethyl group.

Examples of the aromatic hydrocarbon group of 6 to 10 carbon atoms represented by R$^1$ include phenyl, tolyl, xylyl, phenylmethyl, phenylethyl and naphthyl groups. Of these, a phenyl group is preferred as the aromatic hydrocarbon group represented by R$^1$.

The cations included in the ionic liquid of the invention are not particularly limited, and may be monovalent or polyvalent. Monovalent and divalent cations are preferred; monovalent cations are more preferred. The cations may be inorganic cations or may be organic cations.

Examples of inorganic cations include alkali metal ions such as sodium, potassium and lithium ions; and metallic ions such as silver, zinc, copper, calcium, magnesium and barium ions.

Phosphorus atom-containing cations and nitrogen atom-containing cations are preferred as the organic cations. For example, quaternary phosphonium ions, quaternary ammonium ions, imidazolium ions, pyridinium ions, pyrrolidinium ions and piperidinium ions are preferred.

Preferred phosphorus atom-containing cations include quaternary phosphonium ions of formula (2) below.

[Chem. 3]

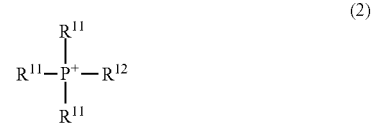

(2)

In formula (2), R$^{11}$ is an alkyl group of 1 to 20 carbon atoms. The alkyl group of 1 to 20 carbon atoms may be linear, branched or cyclic. Specific examples include the above-mentioned alkyl groups of 1 to 14 carbon atoms, and also, for instance, n-pentadecyl, n-hexadecyl, n-heptadecyl, n-octadecyl, n-nonadecyl and n-eicosyl groups.

In formula (2), R$^{12}$ is an alkyl group of 1 to 20 carbon atoms or an alkoxyalkyl goup of the formula —(CH$_2$)$_k$—OR, wherein k is 1 or 2 and R is a methyl group or an ethyl group. The alkyl group of 1 to 20 carbon atoms is exemplified by the same groups as mentioned above in the explanation of R$^{11}$. Examples of the alkoxyalkyl group include methoxymethyl, ethoxymethyl, methoxyethyl and ethoxyethyl groups. Of these alkoxyalkyl groups, a methoxymethyl group or methoxyethyl group is preferred.

Of the quaternary phosphonium ions represented by formula (2), ones in which R$^{12}$ is an alkoxyalkyl group of the formula —(CH$_2$)$_k$—OR tend to form an ionic liquid. When R$^{12}$ is an alkyl group, quaternary phosphonium ions in which R$^{11}$ and R$^{12}$ have differing structures tend to form an ionic liquid. In this case, the difference in the number of carbon atoms is preferably at least 1, more preferably at least 3, and even more preferably at least 5.

The nitrogen atom-containing cation is preferably one represented by formula (3) below.

[Chem. 4]

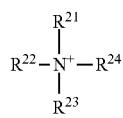
(3)

In formula (3), $R^{21}$ to $R^{24}$ are each independently an alkyl roup of 1 to 20 carbon atoms or an alkoxyalkyl group of the formula —$(CH_2)_k$—OR, wherein R and k are the same as above. The alkyl group of 1 to 20 carbon atoms and the alkoxyalkyl group are exemplified in the same way as in the above explanation of formula (2). In cases where $R^{21}$ to $R^{24}$ are all alkyl groups, nitrogen atom-containing cations in which at least one of these alkyl goups has a structure differing from the others tend to form an ionic liquid. In this case, the difference in the number of carbon atoms is preferably at least 1, more preferably at least 3, and even more preferably at least 5.

Any two of $R^{21}$ to $R^{24}$ may bond with each other and, together with the nitrogen atoms to which they are bonded, form a ring; any two of $R^{21}$ to $R^{24}$ may bond with each other and the remaining two of $R^{21}$ to $R^{24}$ may bond with each other to form respective spiro rings in which the nitrogen atom serves as the spiro atom. Examples of the rings in this case include aziridine, azetidine, pyrrolidine, piperidine, azepane, imidazolidine and morpholine rings. Pyrrolidine and morpholine rings are preferred; pyrrolidine rings are more preferred. A 1,1'-spirobipyrrolidine ring system is especially preferred as the spiro rings.

Specific examples of the nitrogen atom-containing cation of formula (3) include quaternary ammonium ions of formulas (3-1) or (3-2) below, and pyrrolidinium ions of formula (3-3) or (3-4) below.

[Chem. 5]

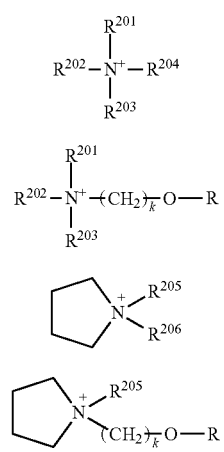

In formulas (3-1) to (3-4), R and k are the same as above, $R^{201}$ to $R^{204}$ are each independently an alkyl group of 1 to 4 carbon atoms, and $R^{205}$ and $R^{206}$ are each independently to an alkyl group of 1 to 4 carbon atoms. Here, nitrogen atom-containing cations in which at least one of $R^{201}$ to $R^{206}$ has a different structure than the others tend to form ionic liquids. In this case, the difference in the number of carbon atoms is preferably one or more. Also, $R^{205}$ and $R^{206}$ may bond with each other and, together with the nitrogen atom to which they are bonded, form a ring.

Imidazolinium ions of formula (4) below are also desirable as the above nitrogen atom-containing cation. [Chem. 6]

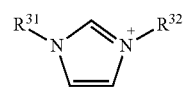
(4)

In formula (4), $R^{31}$ and $R^{32}$ are each independently an alkyl group of 1 to 20 carbon atoms or an alkoxyalkyl group of the formula —$(CH^2)_k$—OR, and R and k are the same as above. The alkyl group of 1 to 20 carbon atoms and the alkoxyalkyl group are exemplified by the same groups as mentioned above in the explanation of formula (2). In this case, imidazolinium ions in which $R^{31}$ and $R^{32}$ are differing groups tend to form an ionic liquid.

Pyridinium ions of formula (5) are also desirable as the nitrogen atom-containing cation. [Chem. 7]

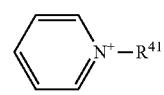
(5)

In formula (5), $R^{41}$ is an alkyl goup of 1 to 8 carbon atoms or an alkoxyalkyl group of the formula —$(CH_2)_k$—OR, and R and k are the same as above. The alkyl goup 1 to 8 carbon atoms may be linear, branched or cyclic. Specific examples include methyl, ethyl, n-propyl, isopropyl, cyclopropyl, n-butyl, s-butyl, isobutyl, t-butyl, cyclobutyl, n-pentyl, n-hexyl, n-heptyl, n-octyl, cyclopentyl and cyclohexyl groups. The alkoxyalkyl group is exemplified by the same groups as mentioned above in the explanation of formula (2).

[Method of Producing Ionic Liquid]

The ionic liquid of the invention can be synthesized according to Scheme A below. [Chem. 8]

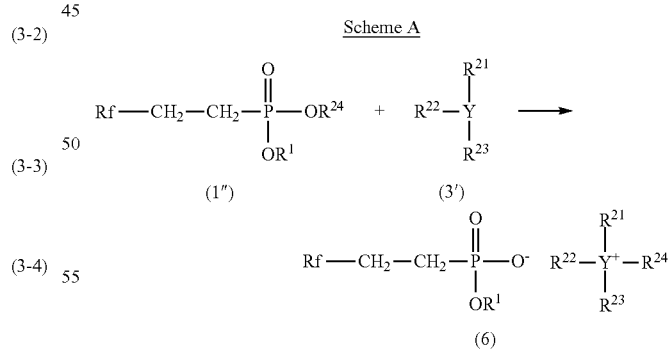

Here, Y is a nitrogen atom or a phosphorus atom. Rf, $R^1$ and $R^{21}$ to $R^{24}$ are as defined above, although it is preferably in this reaction for $R^{24}$ to be an alkyl group of 1 to 4 carbon atoms. That is, in cases where the cation is one of formula (3-2) or formula (3-4), it is preferable to use a compound of formula (1''') below as the compound of formula (1''), and to use a compound of formula (3-2') or formula (3-4') below as the compound of formula (3'). An ionic liquid in which the cations are imidazolium ions of formula (4) or pyridinium ions of formula (5) can be synthesized by a method which is similar to Scheme A but using, in place of the compound of formula (3'), a 1-alkylimidazole or pyridine capable of imparting the above imidazolium ion. Here, because the reaction yields a single product and purification is simple, it is preferable for $R^1$ and $R^{24}$ in formula (1") or $R^1$ and $R^{201}$ in formula (1''') to be the same alkyl group. The compound of formula (3-2') or formula (3-4') below may be synthesized by a known method. [Chem. 9]

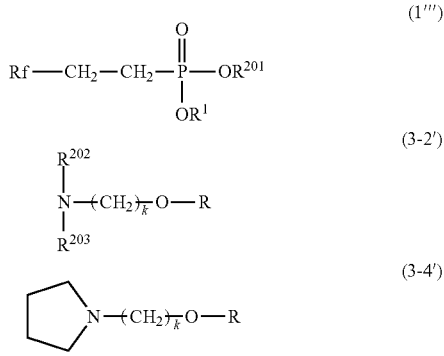

In the formulas, Rf, $R^1$, $R^{201}$ to $R^{203}$, R and k are as defined above.

The ratio in which the compound of formula (1") and the compound of formula (3') are used in carrying out the reaction shown in Scheme A, although not particularly limited is preferably close to 1:1 when taking costs into account. However, to bring the reaction more rapidly to completion, eliminate residual starting materials and simplify the isolation step, the reaction may be carried out using one of these compounds in excess. In such a case, it is preferable to use in excess the ingredient that is easier to remove.

The reaction shown in Scheme A is preferably carried out in the absence of a solvent, although solvents may be used. The solvents that may be used at this time are not particularly limited, so long as it is a solvent which does not impede the reaction. A general-purpose solvent may be suitably used.

The reaction temperature is generally between about 60° C. and about 120° C., and preferably between about 80° C. and about 100° C. The reaction time may be suitably set according to how well the reaction proceeds, and is not particularly limited, although most of the reactants typically react within a period of time ranging from several hours to somewhat under twenty hours. Reaction may be carried out for an even longer time in order to leave behind no residual starting material.

The compound of formula (1") serving as a starting material may be synthesized according to a known method, or a commercial product may be used.

The ionic liquid of the invention can also be produced by a neutralization method which uses any salt that includes a fluorine-containing phosphate ester anion of formula (1) and a salt that includes the above-described cation, and which uses an ion-exchange resin. For example, when synthesizing a salt in which the cation is a quaternary phosphonium ion of formula (2), production may be carried out using an ionic liquid of formula (1') and a salt of formula (2') below [Chem. 10]

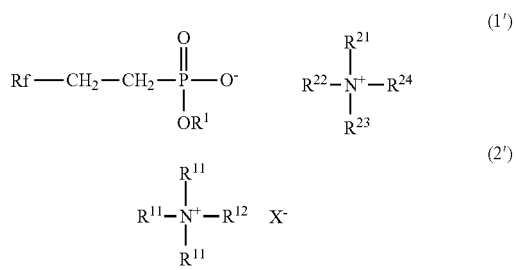

(wherein Rf, $R^1$, $R^{11}$, $R^{12}$ and $R^{21}$ to $R^{24}$ are the same as above, and $X^-$ is any anion).

The ionic liquid of formula (1') may be synthesized by the above-described method. The salt of formula (2') may be synthesized by a known method, or commercial product can be used.

In the case of this neutralization method, first the ionic liquid of formula (1') and the salt of formula (2') may be converted to the fluorine-containing phosphate ester of the formula shown below and to a hydroxide using, respectively, a cation exchange resin and an anion exchange resin, following which the two may be mixed together.

[Chem. 11]

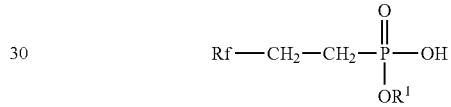

Here, Rf and $R^1$ are the same as above.

In the present invention, when employing this neutralization method, the counterion of the salt of formula (2') is not particularly limited as long as it is ion-exchangeable. However, the counterion is preferably a halide ion, with a chloride ion or a bromide ion being especially preferred from the standpoint of cost. The salt of formula (1') above is an ammonium salt and the salt of formula (2') is a phosphonium salt. However, the type of cation is not limited; use can be made of a salt having any cation. In particular, instead of the salt of formula (2'), use can be made of a salt having the cation of the ionic liquid that one wishes to synthesize. Ammonium salts having a cation of formula (3), imidazolium salts having a cation of formula (4), and pyrrolidinium salts having a cation of formula (5) can of course be used.

Although the used ratio of the fluorine-containing phosphate ester and the hydroxide in the neutralization reaction is not particularly limited, the molar ratio can be set to generally from about 5:1 to about 1:5. From the standpoint of cost considerations, it is preferable to carry out the reaction at a ratio close to 1:1, and it is especially preferable to have the neutralization point of the aqueous phase be the reaction endpoint. Following reaction completion, the target substance can be obtained by carrying out the usual workup.

An example of another method for producing the ionic liquid is one that uses an ionic liquid of formula (1') and a salt of formula (2') and carries out ion exchange using an ion exchange resin.

This ion exchange method specifically involves first passing an aqueous solution of the salt of formula (1') through a column packed with a cation exchange resin, causing the cations of this salt to be supported on the cation exchange resin, and then washing the column by passing water through. Next, by passing the salt of formula (2') through the column and collecting and purifying the eluate, the target ionic liquid can be produced. Here, as mentioned above, the types of cation in the salt of formula (1') and the salt of formula (2') are not limited; use can be made of salts having any cations. In particular, it is desirable to use a salt having the cation of the ionic liquid one wishes to synthesize instead of the salt of formula (2').

The cation exchange resin that is used may be a commonly used cation exchange resin, although it is preferable to use a strongly acidic cation exchange resin. Such resins may be acquired as commercial products.

Aside from the above synthesis methods, it is also possible to synthesize the ionic liquid of the invention by common ionic liquid synthesis methods described in publications such as *Ion-sei Ekitai-Kaihatsu no Saizensen to Mirai*-[Ionic liquids-the frontier and future of development], CMC Publishing (2003) and *Ion Ekitai II-Kyōiteki na Shinpo to Tasai na Kinmirai*-[Ionic liquids II-amazing progress and multifaceted near-future], CMC Publishing (2006). For example, production may be carried out by reacting a salt of formula (2') with an ionic liquid of formula (1') in a solvent. In this case, the solvent may be either water or an organic solvent. The solvent should be suitably selected while taking into account, for example, the ease of isolating and purifying the product.

[Lubricating Oil Composition]

The lubricating oil composition of the invention includes the above ionic liquid. Because the ionic liquid has a low fiction coefficient that varies little, it can be suitably used as the base oil in a lubricating oil composition.

The lubricating oil composition may be one that consists only of the ionic liquid, or it may include additives that are commonly used as lubricating oil additives. Examples of such additives include oxidation inhibitors, antifoam agents, demulsifying agents, emulsifying agents, preservatives, viscosity index improvers, pour point depressants, oiliness agents, antiwear agents, extreme pressure agents, friction modifiers, detergents, dispersants, rust preventives, corrosion inhibitors, colorants and dyes.

Examples of oxidation inhibitors include phenol derivatives, aromatic amine derivatives, organosulfur compounds, organophosphorus compounds, zinc dithiophosphate and hindered amines. When an oxidation inhibitor is included, the content thereof in the lubricating oil composition is preferably from 0.1 to 10 wt %.

Examples of antifoam agents include organopolysiloxanes (dimethylpolysiloxane, etc.) and polyacrylate derivatives. When an antifoam agent is included, the content thereof in the lubricating oil composition is preferably from 0.1 to 10 wt %.

Examples of demulsifying agents include ethylene oxide and propylene oxide polymers, ether-type surfactants, and ester-type surfactants. When a demulsifying agent is included, the content thereof in the lubricating composition is preferably form 0.1 to 10 wt %.

Examples of emulsifying agents include metal salts such as sulfonates, and surfactants such as fatty acid amine salts. When an emulsifying agent is included, the content thereof in the lubricating composition is preferably from 0.1 to 10 wt %.

Examples of preservatives include formaldehyde emitters, pyridine-type compounds and phenolic compounds. When a preservative is included, the content thereof in the lubricating oil composition is preferably from 0.1 to 10 wt %.

Examples of viscosity index improvers include polyalkyl methacrylates, olefin copolymers (e.g., ethylene-propylene copolymers), polyisobutylene, styrene-butadiene block copolymers, graft copolymers of polyalkyl methacrylates and olefin copolymers, and hydrogenated radial isoprene polymers. When a viscosity index improver is included, the content thereof in the lubricating oil composition is preferably from 0.1 to 10 wt %.

Examples of pour point depressants include alkylated aromatic compounds such as polyalkyl methacrylates, polyalkyl acrylates and alkyl naphthalenes; and fumaric acid ester-vinyl acetate copolymers, styrene-maleic anhydride ester copolymers and ethylene-vinyl acetate copolymers. When a pour point depressant is included, the content thereof in the lubricating oil composition is preferably from 0.1 to 10 wt %.

Examples of oiliness agents include alcohols, long-chain fatty acids, alkyl amines, ester compounds and amide compounds. When an oiliness agent is included, the content thereof in the lubricating oil composition is preferably from 0.1 to 10 wt %.

Examples of antiwear agents include zinc dithiophosphate and organophosphorus compounds. When an antiwear agent is included, the content thereof in the lubricating oil composition is preferably from 0.1 to 10 wt %.

Examples of extreme pressure agents include organosulfur compounds and amine salts of phosphate esters. When an extreme pressure agent is included, the content thereof in the lubricating oil composition is preferably from 0.1 to 10 wt %.

Examples of friction modifiers include esters of long-chain fatty acids such as oleic acid (e.g., glycerol monooleate), long-chain amide compounds, and organomolybdenum compounds such as molybdenum dithiocarbamate. When a friction modifier is included, the content thereof in the lubricating oil composition is preferably from 0.1 to 10 wt %.

Examples of detergents include neutral and perbasic metal salts (calcium salts, magnesium salts, barium salts, etc.) of alkyl benzene sulfonates, alkyl phenates and alkyl salicylates. When a detergent is included, the content thereof in the lubricating oil composition is preferably from 0.1 to 10 wt %.

Examples of dispersants include succinimides having an lipophilic group and a polar group, such as polybutenyl succinimide, succinic acid esters, benzylamine and polyamine. When a dispersant is included, the content thereof in the lubricating oil composition is preferably from 0.1 to 10 wt %.

Examples of rust preventives include metal salts such as sulfonates, carboxylic acid ester compounds of polyhydric alcohols, phosphate ester compounds, alkenyl succinic acid derivatives, carboxylic acid salts and amine compounds. When a rust preventive is included the content thereof in the lubricating oil composition is preferably from 0.1 to 10 wt %.

Examples of corrosion inhibitors include benzotriazole derivatives and thiadiazole derivatives. When a detergent is included, the content thereof in the lubricating oil composition is preferably from 0.1 to 10 wt %.

Examples of colorants include oil-soluble colorants. When a colorant is included, the content thereof in the lubricating oil composition is preferably from 0.1 to 10 wt %.

Examples of fragrances include oil-soluble fragrances. When a fragrance is included, the content thereof in the lubricating oil composition is preferably from 0.1 to 10 wt %.

These additives may be of one type used alone, or two or more types may be used in combination. When a plurality of such additives are included, the sum of the additives is preferably not more than 30 wt % of the lubricating oil composition.

EXAMPLES

Examples and Comparative Examples are given below by way of illustration, although the invention is not limited by these Examples.

[1] Synthesis of Ionic Liquids

[Example 1] Synthesis of EMEP·FHP-E

[Chem. 12]

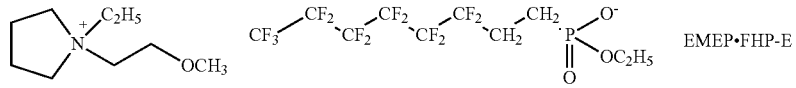

Figure 2:
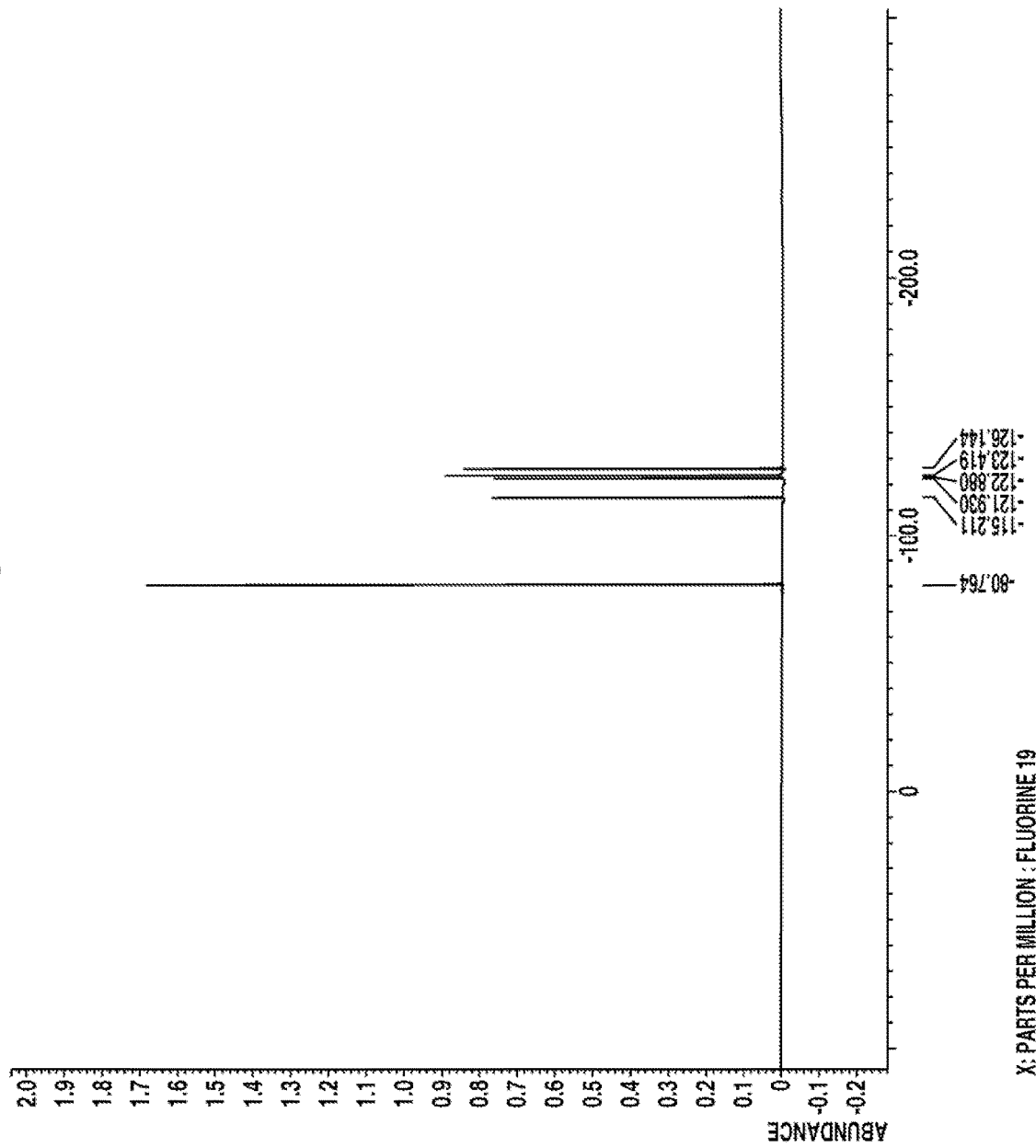
FIG. 2 is a $^{19}$F-NMR spectrum of EMEP·FHP-E produced in Example 1.
Figure 3:
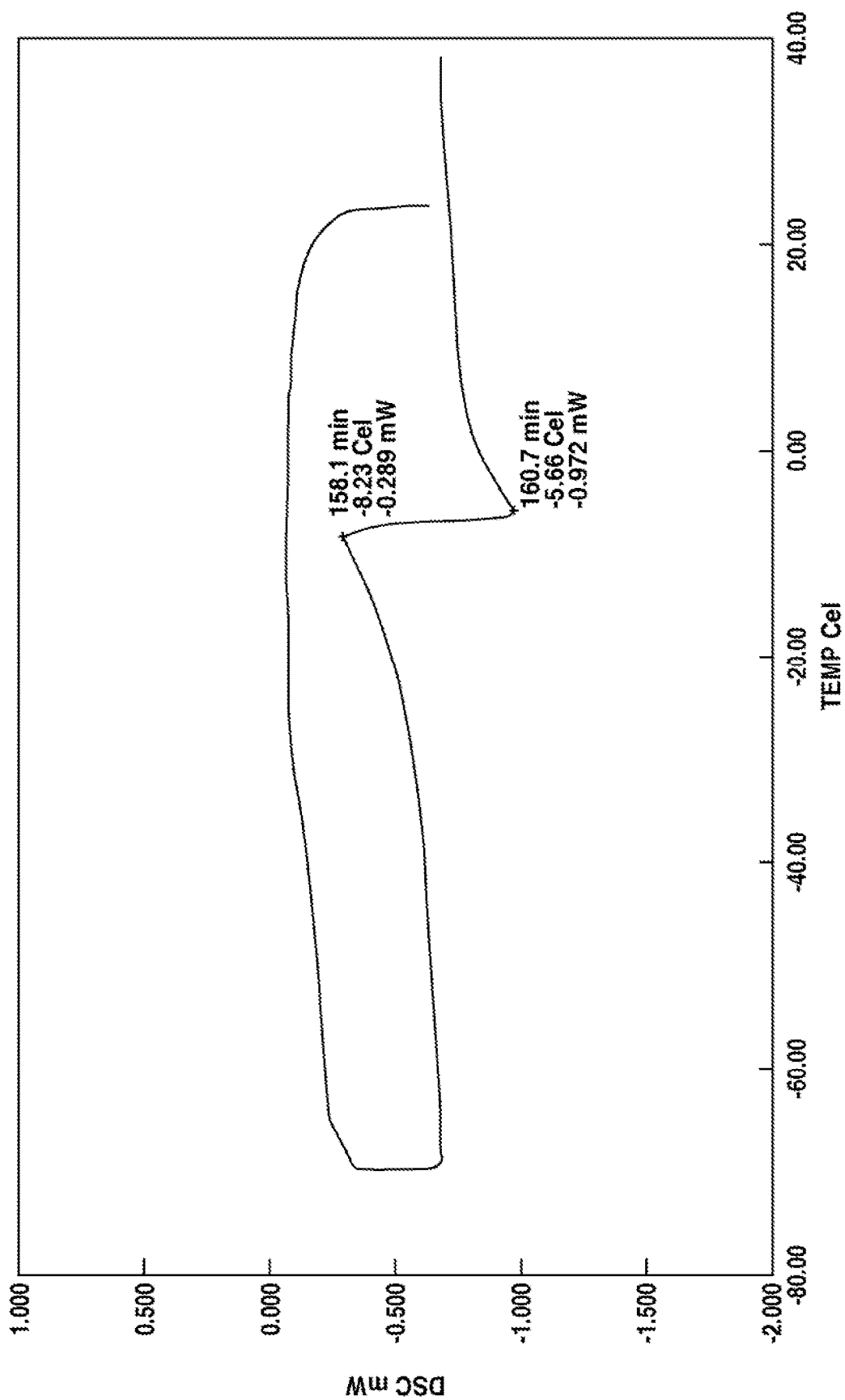
FIG. 3 is a DSC chart of EMEP·FHP-E produced in Example 1.

An autoclave reactor was charged with 59.52 parts by weight of N-2-methoxyethylpyrrolidine synthesized by the same method as in Synthesis Example 1 in JP-A 2016-119801 and 43.36 parts by weight of FHP-EE (Unimatec Co., Ltd.) and, with the reactor closed, the contents were reacted under stirring at 140° C. and 800 rpm for 16.5 hours. Following reaction, the reaction mixture separated into two phases. The top phase was yellow in color and the bottom phase was dark brown. Using tetrahydrofuran (Kanto Chemical Co., Ltd.) as a washing fluid, the reaction mixture was transferred to a round-bottomed flask, after which the tetrahydrofuran was driven off with an evaporator. Next, 66 parts by weight of hexane (Kanto Chemical Co., Ltd.) was added and the flask contents were stirred, following which the system was left at rest and separated into two phases, the top phase of which was removed by decantation. This operation was repeated two more times, thereby washing the bottom phase. Using 66 parts by weight of a mixed solution of tetrahydrofuran and hexane (1:3) instead of hexane, the bottom phase was washed another two times in the same way as described above. The solvent was removed with an evaporator, following which vacuum pumping was carried out under stirring, giving 35.89 parts by weight of the target substance EMEP·FHP-E as a clear orange liquid (melting point, −5° C.). FIG. 1 shows the $^1$H-NMR chart for EMEP·FHP-E (solvent: deuterated chloroform), FIG. 2 shows the $^{19}$F-NMR chart (solvent, deuterated chloroform), and FIG. 3 shows the DSC chart.

[Example 2] Synthesis of BDDP·FHP-E [Chem. 13]

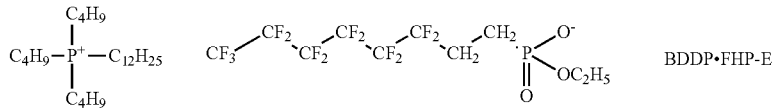

Figure 4:
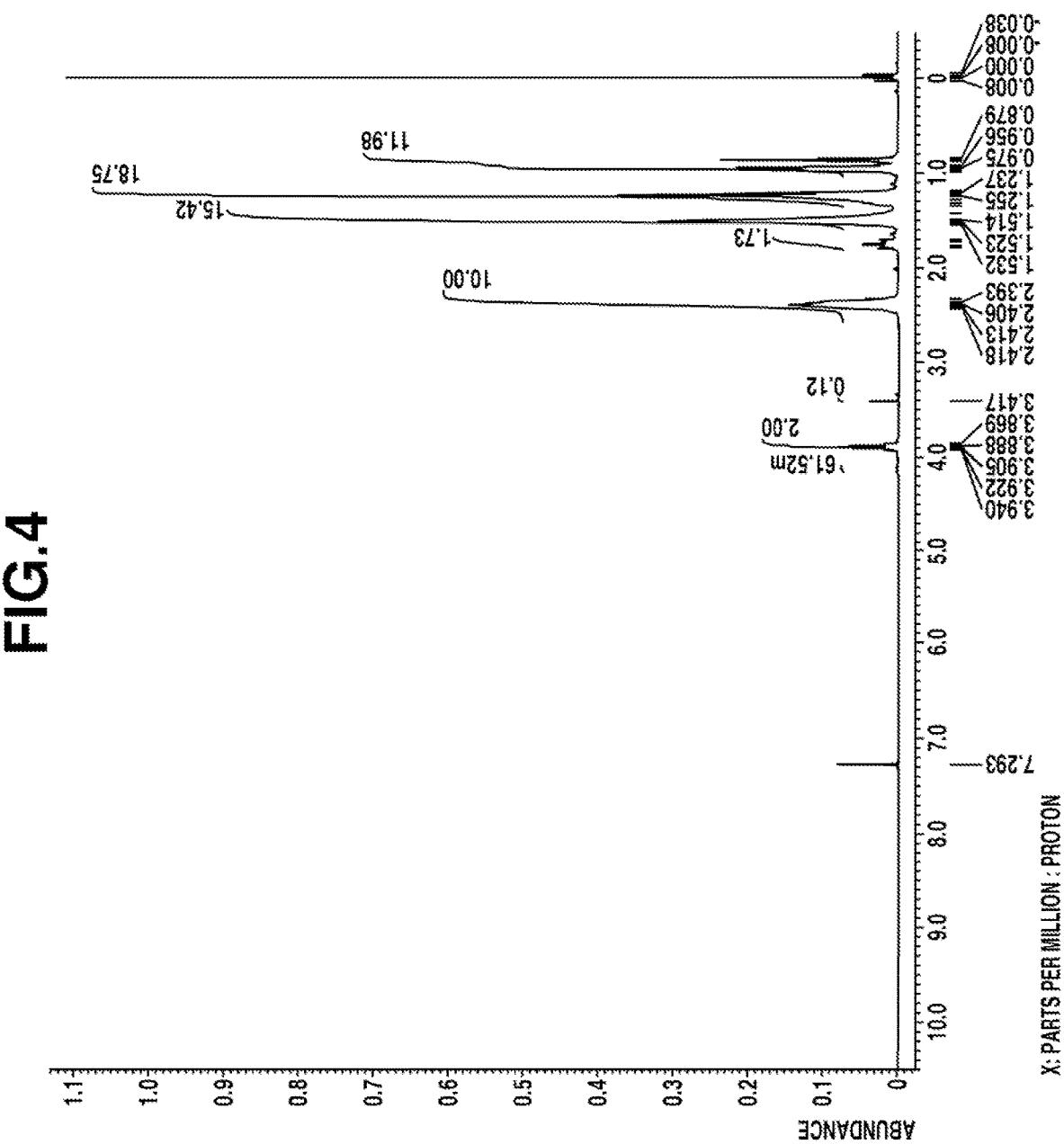
FIG. 4 is a $_1$H-NMR spectrum of BDDP·FHP-E produced in Example 2.
Figure 5:
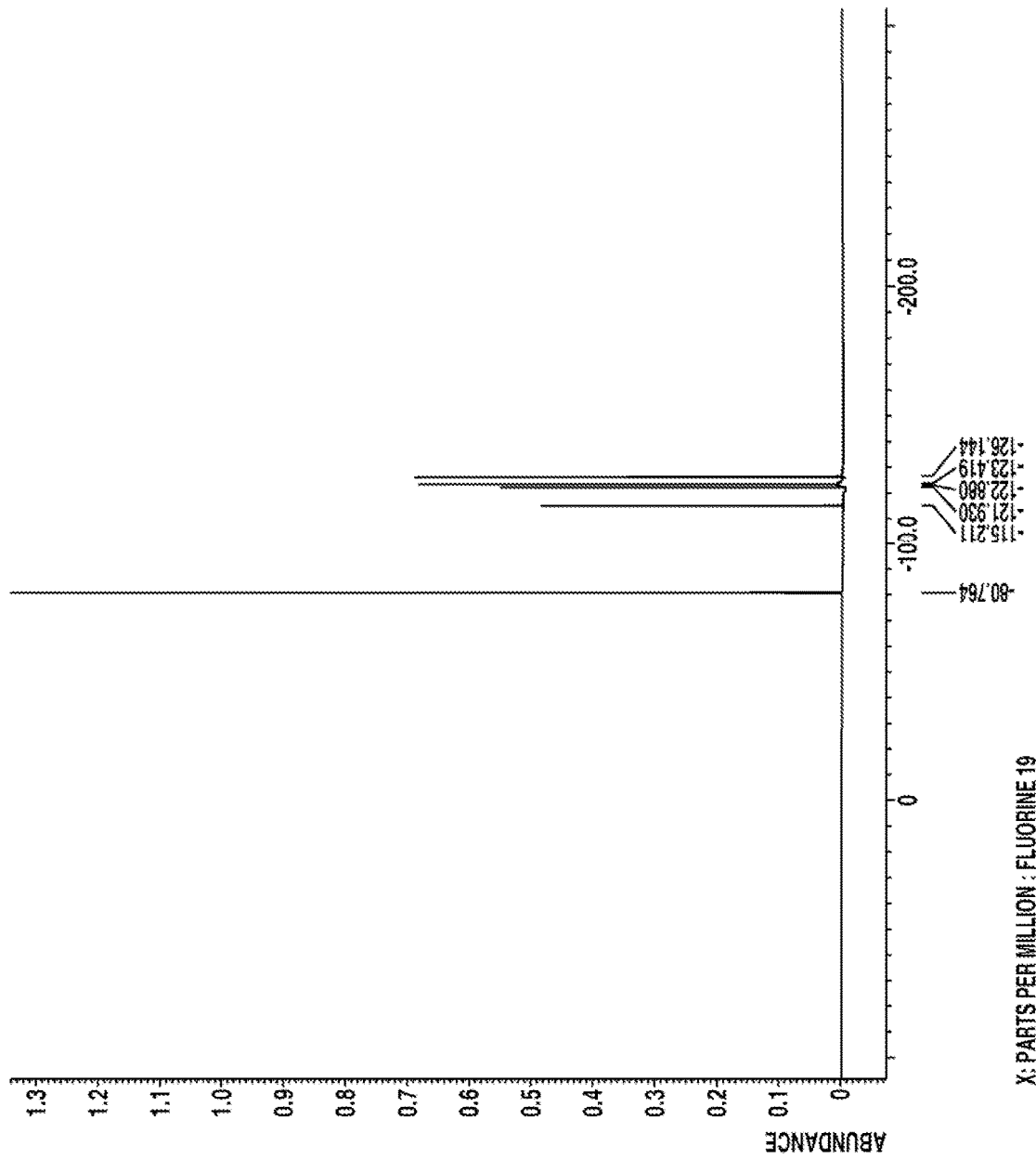
FIG. 5 is a $_{19}$F-NMR spectrum of BDDP·FHP-E produced in Example 2.
Figure 6:
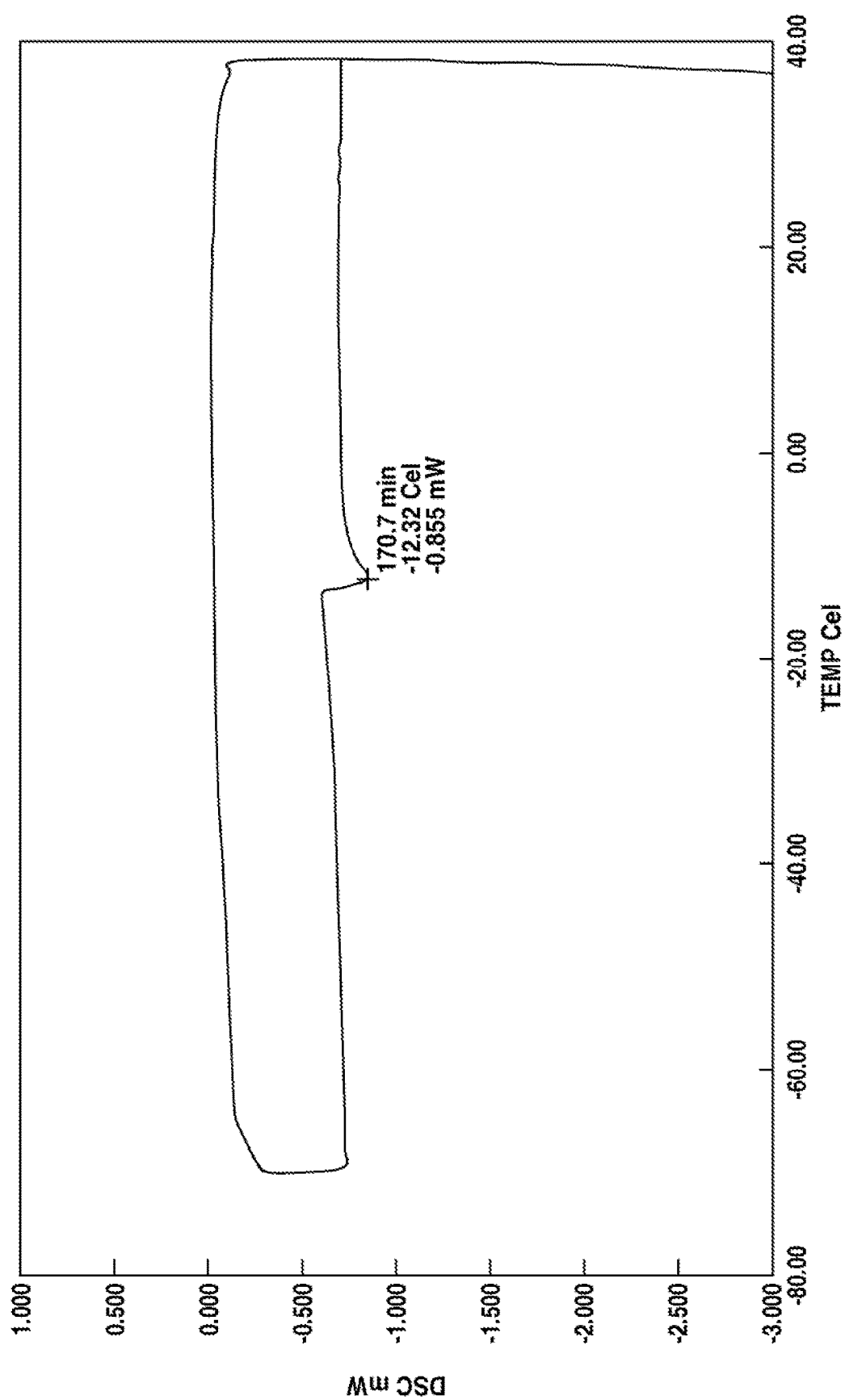
FIG. 6 is a DSC chart of BDDP·FHP-E produced in Example 2.

A uniform solution was prepared by placing 9.2 parts by weight of EMEP·FHP-E in a round-bottomed flask, adding 50 parts by weight of deionized water and stirring the flask contents. Next, 12.2 parts by weight of a 50 wt % aqueous solution of tributyldodecylphosphonium chloride (Nippon Chemical Industrial Co., Ltd.) was added and the flask contents were stirred for 30 minutes. Following the end of stung, 90 parts by weight of ethyl acetate (Kanto Chemical Co., Ltd.) was added to the cloudy reaction mixture and the mixture was stirred for another 6 hours. The reaction mixture was transferred to a separatory funnel, the bottom phase (aqueous phase) obtained with separation of the system into two phases after being left at rest was removed, the top phase (organic phase) was transferred to a round-bottomed flask and 50 parts by weight of deionized water was added. Next, 1.84 parts by weight of EMEP·FHP-E was added to this mixture and stirring was carried out overnight. The reaction mixture was transferred to a separatory funnel, the bottom phase (aqueous phase) obtained with separation of the system into two phases after being left at rest was removed, 20 parts by weight of deionized water was added to the top phase, and washing was carried out three times. The top phase was concentrated with an evaporator, following which vacuum pumping was carried out under stirring, giving 11.74 parts by weight of the target substance BDDP·FHP-E as a clear, light yellow liquid (melting point, −12° C.). FIG. 4 shows the $^1$H-NMR chart for BDDP·FHP-E (solvent: deuterated chloroform), FIG. 5 shows the $^{19}$F-NMR chart (solvent, deuterated chloroform), and FIG. 6 shows the DSC chart.

[Example 3] Synthesis of BHDP·FHP-E [Chem. 14]

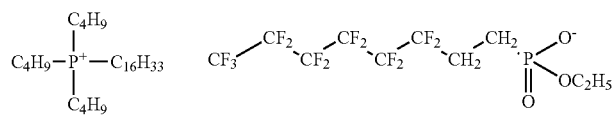

BHDP·FHP-E

Figure 7:
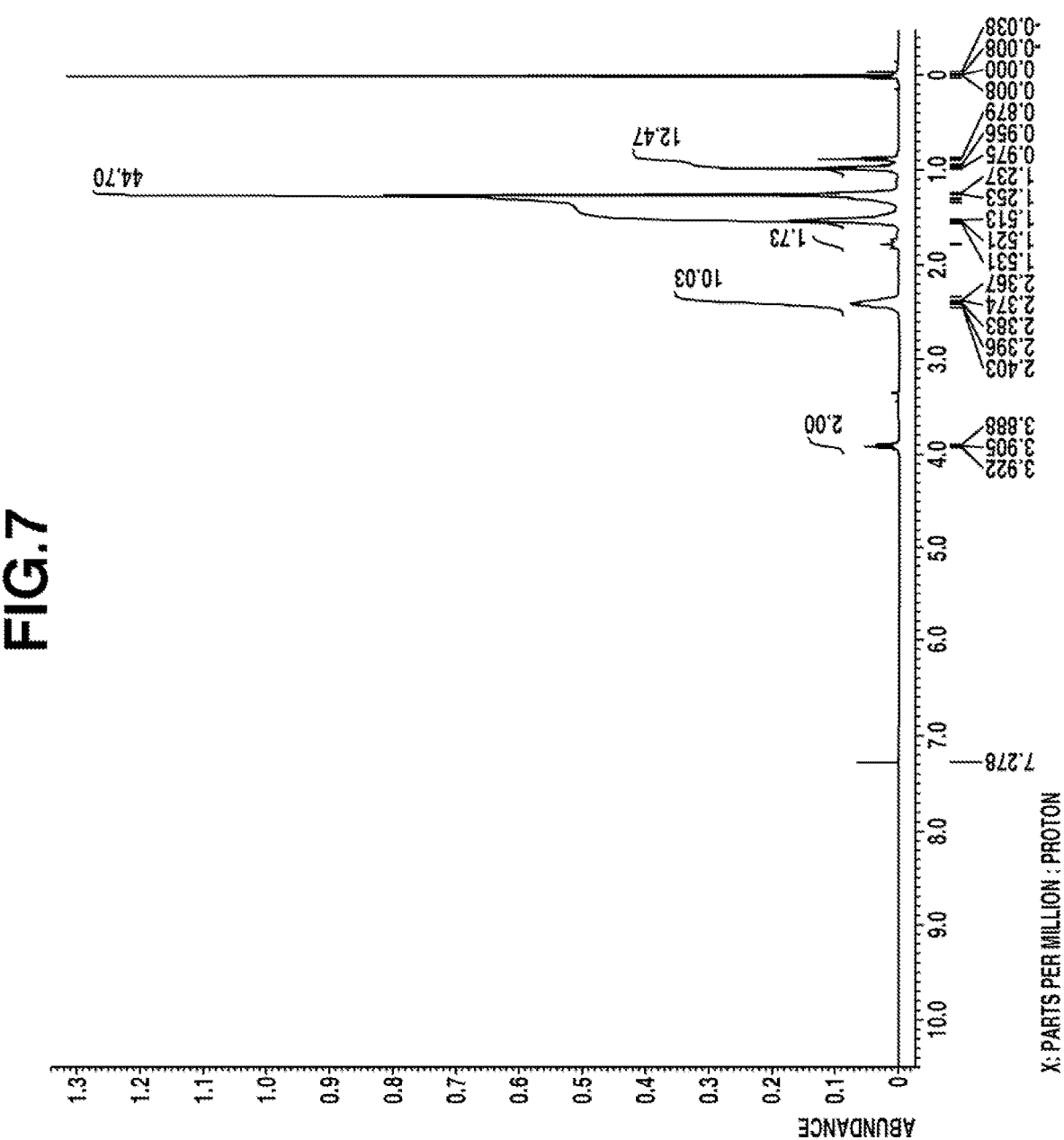
FIG. 7 is a $^1$H-NMR spectrum of BHDP·FHP-E produced in Example 3.
Figure 8:
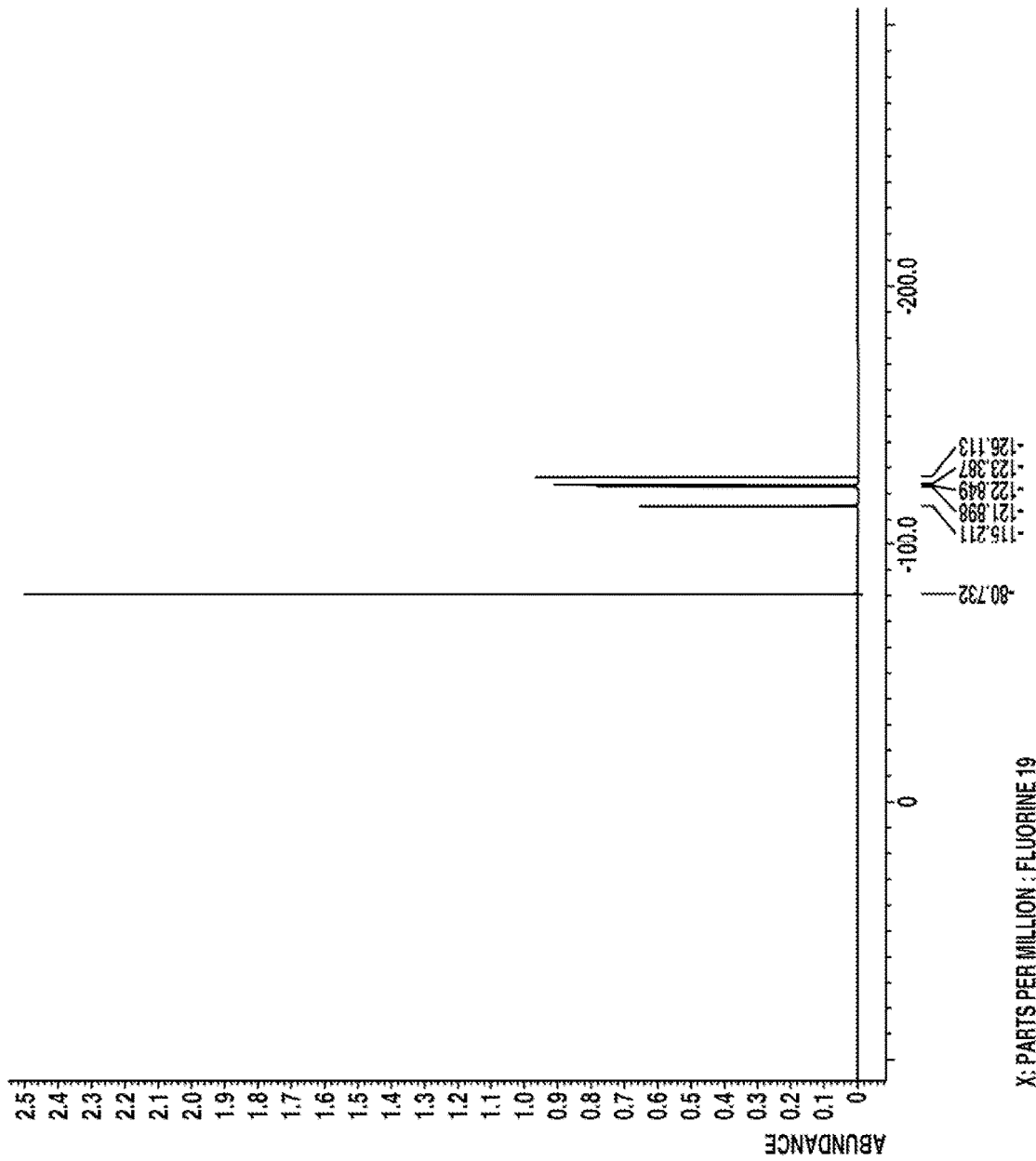
FIG. 8 is a $^{19}$F-NMR spectrum of BHDP·FHP-E produced in Example 3.
Figure 9:
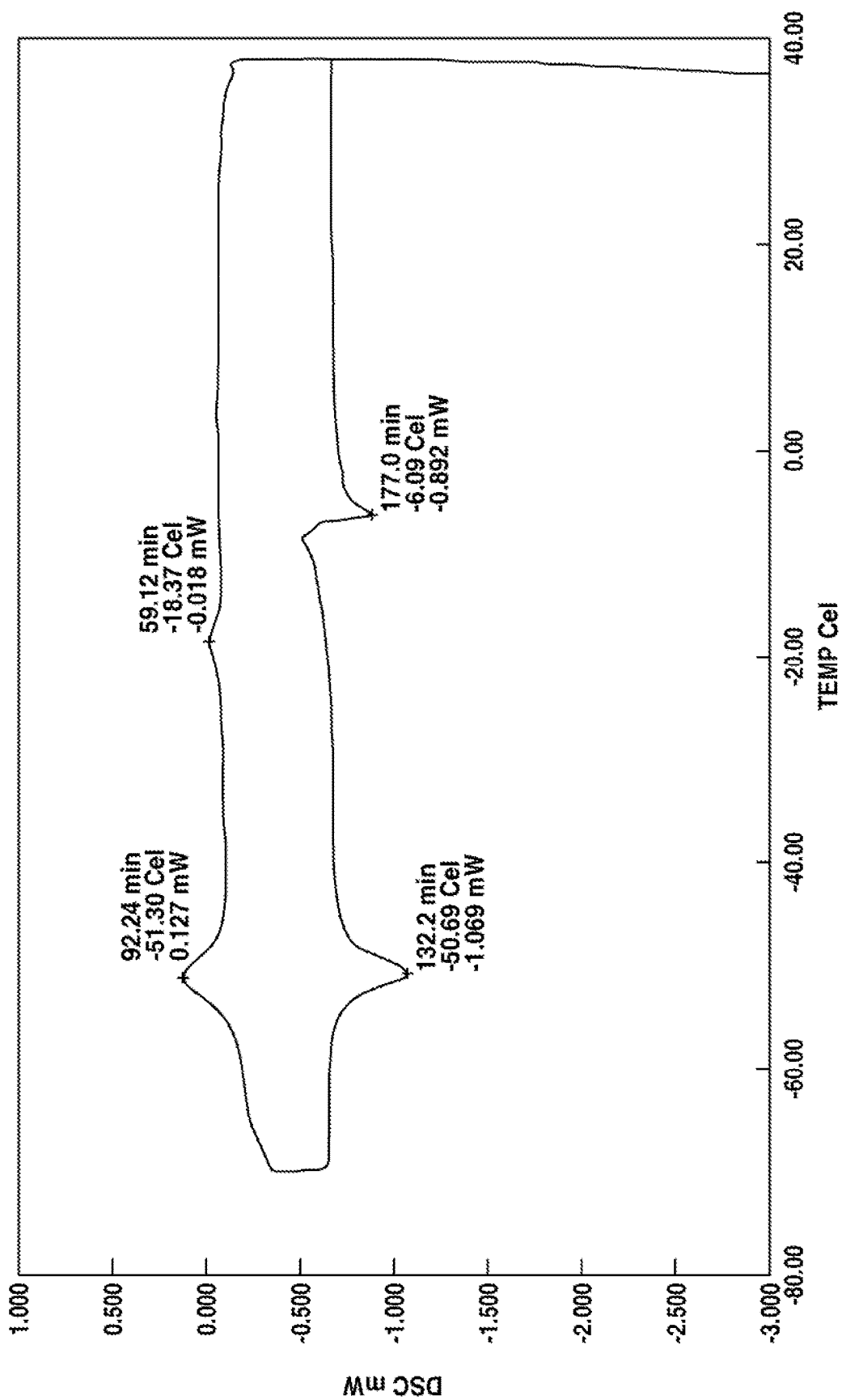
FIG. 9 is a DSC chart of BHDP·FHP-E produced in Example 3.

Aside from replacing the 50 wt % aqueous solution of tributyldodecylphosphonium chloride with a 50 wt % aqueous solution of tributylhexadecylphosphonium chloride (Nippon Chemical Industrial Co., Ltd.), BHDP·FHP-E was obtained in a yield of 88% as a clear, light-yellow liquid (melting point, −6° C.) by the same method as in Synthesis Example 2. FIG. 7 shows the $^1$H-NMR chart for BHDP·FHP-E (solvent: deuterated chloroform), FIG. 8 shows the $^{19}$F-NMR chart (solvent, deuterated chloroform), and FIG. 9 shows the DSC chart. [Example 4] Synthesis of EMI·FHP-E [Chem. 15]

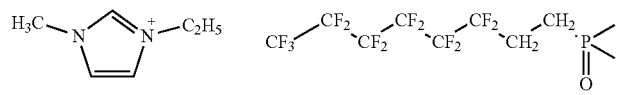

EMI·FHP-E

Figure 10:
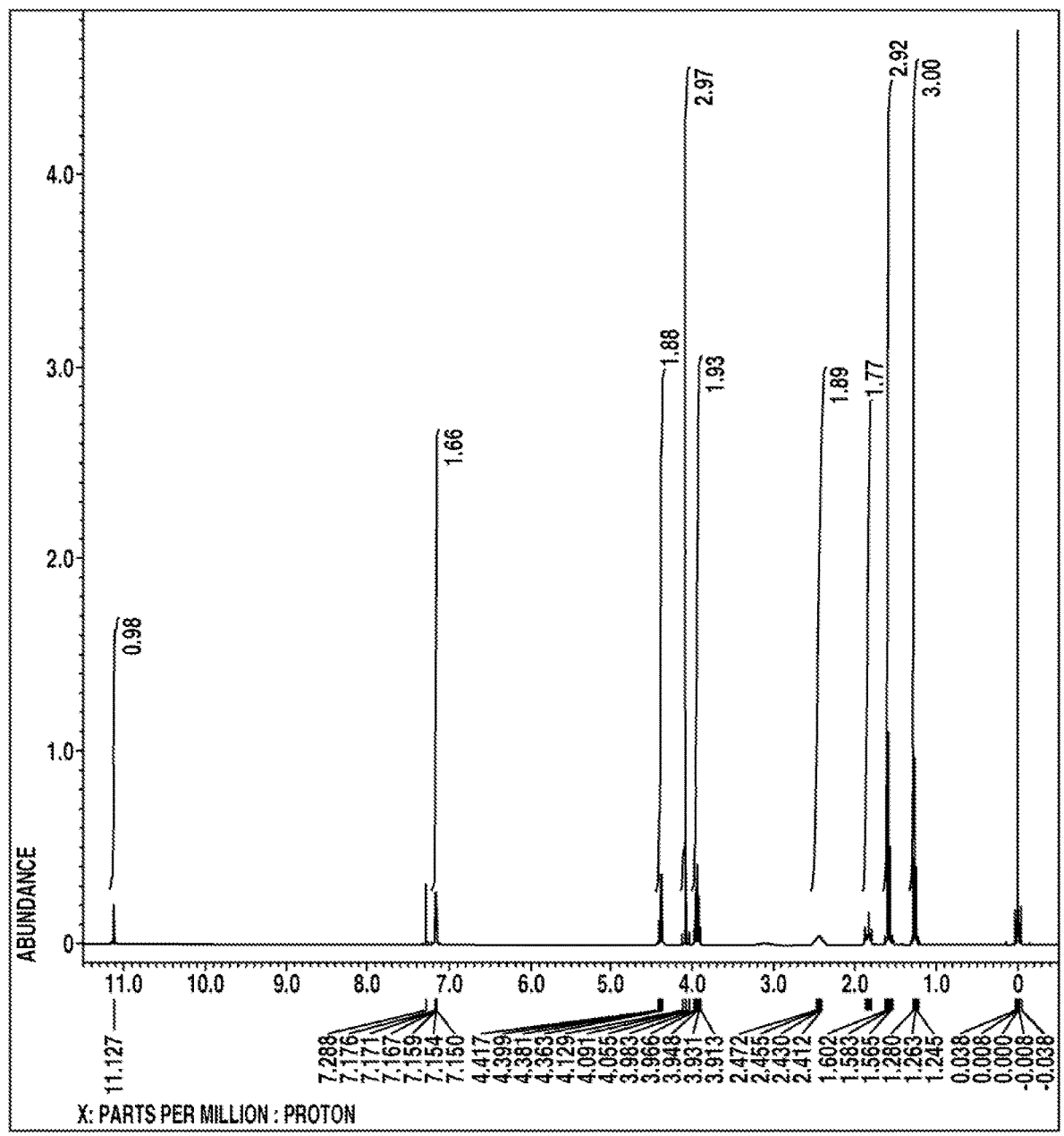
FIG. 10 is a $^1$H-NMR spectrum of EMI·FHP-E produced in Example 4.
Figure 11:
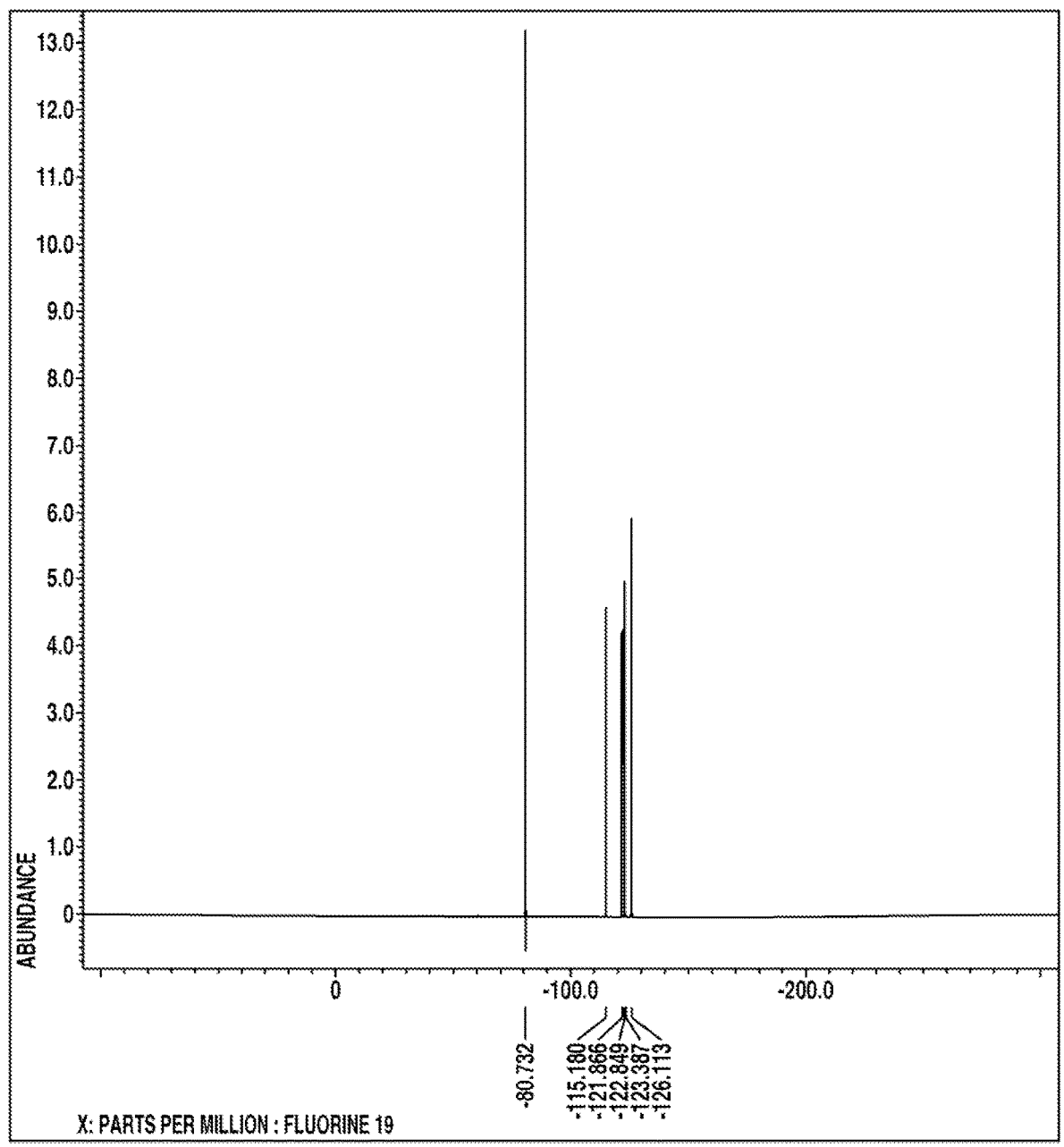
FIG. 11 is a $^{19}$F-NMR spectrum of EMI·FHP-E produced in Example 4.
Figure 12:
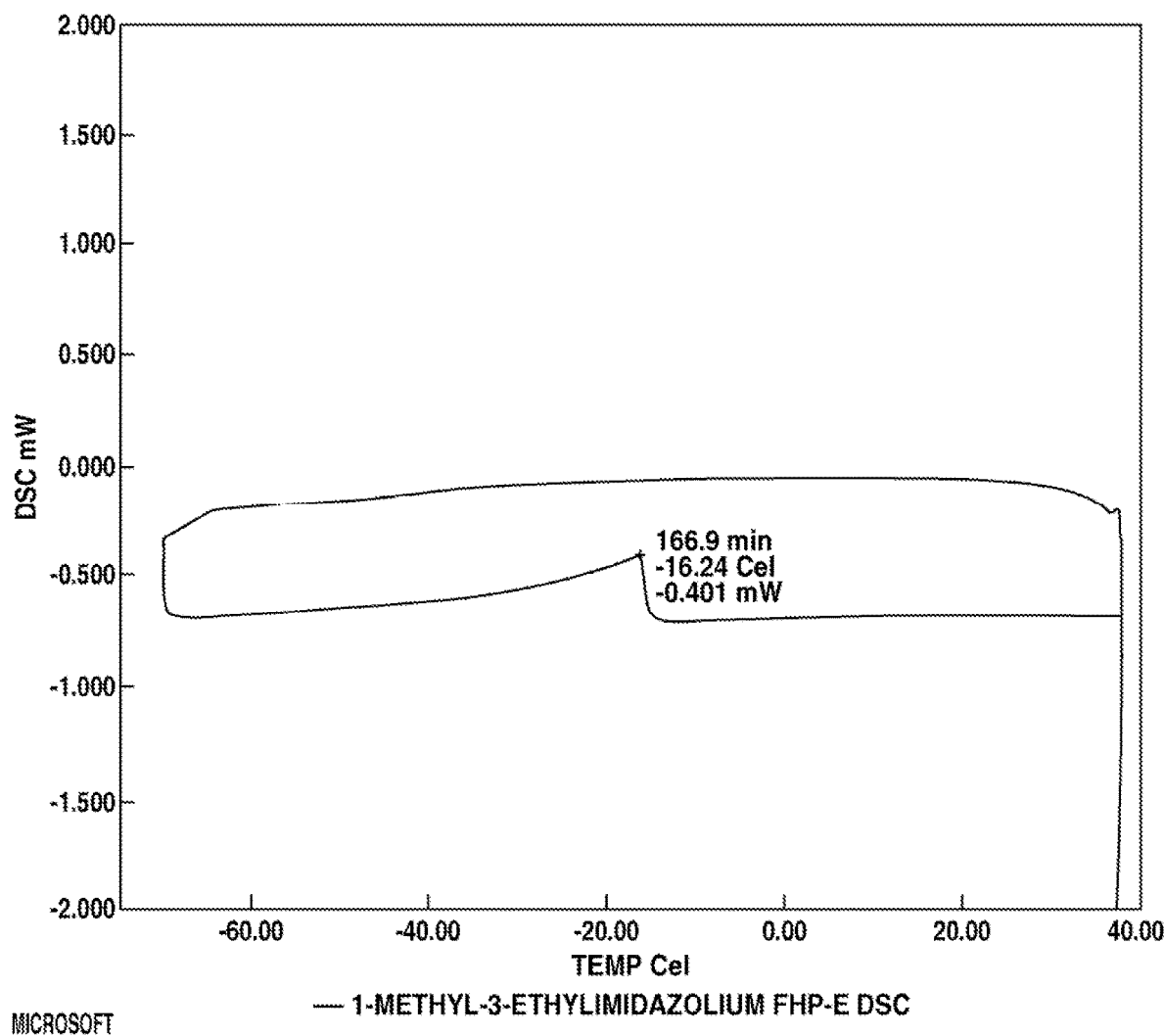
FIG. 12 is a DSC chart of EMI·FHP-E produced in Example 4.

Aside from replacing N-2-methoxyethylpyrrolidine with methyl imidazole (Kanto Chemical Co., Ltd.), EMI·FHP-E was obtained in a yield of 88% as a clear orange liquid (melting point, −16° C.) by the same method as in Synthesis Example 1. FIG. 10 shows the $^1$H-NMR chart for EMI·FHP-E (solvent: deuterated chloroform), FIG. 11 shows the $^{19}$F-NMR chart (solvent, deuterated chloroform), and FIG. 12 shows the DSC chart.

[2] Friction Test

A friction test (ball-on-disk, direct-drive system) was carried out under the following conditions on the ionic liquids in Examples 1 to 3 and, as Comparative Examples, the ionic liquid 1-butyl-3-methylimidazolinium bis(trifluoromethanesulfonyl)amide (BMI·TFSA, from Kanto Chemical Co., Ltd.) and YUBASE4 (from SK Lubricants).

| | |
|---|---|
| Measuring apparatus: | HEIDON TYPE 40 (Shinto Kagaku KK) |
| Conditions: | Sliding speeds: 0.5, 1, 5, 10, 30 and 50 mm/sec Load: 100 gf (1N) |
| Materials: | Ball: glass ball Disk: silicon wafer |

FIG. 13 shows the relationship between the friction coefficients for the ionic liquids of Examples 1 to 3 and the ionic liquid and YUBASE4 of the Comparative Examples. From these results, it is apparent that the ionic liquids of the invention had low friction coefficients and were suitable as base oils for lubricating oil compositions.

The invention claimed is:
1. An ionic liquid comprising fluorine-containing phosphate ester anions of formula (1) below

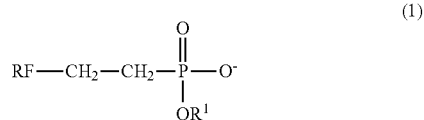 (1)

(wherein Rf is a perfluoroalkyl group of 1 to 14 carbon atoms, and $R^1$ is an alkyl group of 1 to 8 carbon atoms or an aromatic hydrocarbon group of 6 to 10 carbon atoms).

2. The ionic liquid of claim 1, wherein Rf is a linear perfluoroalkyl group of 1 to 14 carbon atoms.

3. The ionic liquid of claim 2, wherein Rf is a perfluoroethyl, perfluoro-n-butyl, perfluoro-n-hexyl, perfluoro-n-octyl, perfluoro-n-decyl, perfluoro-n-dodecyl or perfluoro-n-tetradecyl group.

4. The ionic liquid of claim 1, wherein $R^1$ is an alkyl group of 1 to 4 carbon atoms.

5. The ionic liquid of claim 1, wherein $R^1$ is a group of 6 to 8 carbon atoms which includes a phenyl group.

6. The ionic liquid of claim 1, wherein the ionic liquid further comprises phosphorus atom-containing cations.

7. The ionic liquid of claim 1, wherein the ionic liquid further comprises nitrogen atom-containing cations.

8. The ionic liquid of claim 1 which has a melting point of 50° C. or below.

9. The ionic liquid of claim 8, wherein the melting point is 25° C. or below.

10. A lubricating oil composition comprising the ionic liquid of claim 1.

11. The lubricating oil composition of claim 10, wherein the ionic liquid serves as a base oil.

12. The lubricating oil composition of claim 11, further comprising at least one type of additive selected from the group consisting of oxidation inhibitors, antifoam agents, denuilsifying agents, emulsifying agents, preservatives, viscosity index improvers, pour point depressants, oiliness agents, antiwear agents, extreme pressure agents, friction modifiers, detergents, dispersants, rust preventives, corrosion inhibitors, colorants and fragances.

* * * * *